(12) United States Patent
Karp et al.

US008404656B2

(10) Patent No.: US 8,404,656 B2
(45) Date of Patent: Mar. 26, 2013

(54) METHODS OF TREATMENT AND PREVENTION OF DIET-INDUCED OBESITY AND SEQUELAE THEREOF

(75) Inventors: Christopher L. Karp, Cincinnati, OH (US); Stuart P. Weisberg, New York, NY (US); Senad Divanovic, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 12/672,869

(22) PCT Filed: Aug. 11, 2008

(86) PCT No.: PCT/US2008/072782
§ 371 (c)(1),
(2), (4) Date: May 3, 2011

(87) PCT Pub. No.: WO2009/021234
PCT Pub. Date: Feb. 12, 2009

(65) Prior Publication Data
US 2011/0200580 A1    Aug. 18, 2011

Related U.S. Application Data

(60) Provisional application No. 60/964,084, filed on Aug. 9, 2007.

(51) Int. Cl.
C12N 15/11    (2006.01)
C12N 15/00    (2006.01)
C07H 21/02    (2006.01)
(52) U.S. Cl. .................... 514/44 A; 536/24.5; 435/320.1
(58) Field of Classification Search .................... None
See application file for complete search history.

(56) References Cited

U.S. PATENT DOCUMENTS

| 2004/0018972 A1 | 1/2004 | Gorczynski et al. |
| 2004/0110146 A1* | 6/2004 | Dobie ............................... 435/6 |
| 2005/0238650 A1 | 10/2005 | Crowley et al. |
| 2006/0292119 A1 | 12/2006 | Chen et al. |

FOREIGN PATENT DOCUMENTS

| WO | WO 00/12130 A1 | 3/2000 |
| WO | WO 2005/110470 A2 | 11/2005 |
| WO | WO 2006/102408 A2 | 9/2006 |

OTHER PUBLICATIONS

Hadidi et al (Transplantation 73(11): 1771-1779, 2002).*
Cani et al., 2007, "Metabolic endotoxemia initiates obesity and insulin resistance," Diabetes 56(7): 1761-1762.
Divanovic et al., 2005, "Negative regulation of Toll-like receptor 4 signaling by the Toll-like receptor homolog RP105," Nature Immunol. 6: 571-578.
Gorczynski et al., 2000, "Regulation of gene expression of murine MD-1 regulates subsequent T cell activation and cytokine production," J Immunol. 165(4):1925-32.
Kim et al., 2007, "Toll-like receptor-4 mediates vascular inflammation and insulin resistance in diet-induced obesity," Ciro Res 100(11), pp. 1589-1596.
Koarada et al., 2001, "CD180 (RP105) in rheumatic diseases," Rheumatology 40(11): 1315-1321.
Nagai et al., 2005, "The radioprotective 105/MD-1 complx links TLR2 and TLR4/MD-2 in antibody response to microbial membranes," J Immunol 174(11), pp. 7043-7049.
Nagai et al., 2002, "Requirement for MD-1 in cell surface expression of RP105/CD180 and B-cell responsiveness to lipopolysaccharide," Blood 99, 1699-1705.
Ogata et al., 2000, "The toll-like receptor protein RP105 regulates lipopolysaccharide signaling in B cells," J. Exp. Med. 192, 23-30.
Ohnishi et al., 2001, "N-linked glycosylations at Asn(26) and Asn(114) of human MD-2 are required for toll-like receptor 4-mediated activation of NF-kappaB by lipopolysaccharide," J. Immunol. 167: 3354-3359.
Sequence Accession No. BC038846, 2006.
Sequence Accession No. NM_005582, 2010.
Shi et al., 2006, "TLR4 links innate immunity and fatty acid-induced insulin resistance," J. Clin. Invest 116: 3015-3025.
Shoelson et al., 2006, "Inflammation and insulin resistance," J. Clin. Invest. 116: 1793-1801.
Tsukumo et al., 2007, "Loss-of-function mutation in Toll-like receptor 4 prevents diet-induced obesity and insulin resistance," Diabetes 56(8): 1986-1998.

* cited by examiner

Primary Examiner — Richard Schnizer
(74) Attorney, Agent, or Firm — Davis Wright Tremaine LLP

(57) ABSTRACT

Disclosed are methods of treating or preventing diet-induced obesity and/or one or more sequelae thereof in a subject. These methods comprise administering to a subject in need of treatment or at risk for developing diet-induced obesity and/ or one or more sequelae thereof, a therapeutically effective amount of a pharmaceutical composition comprising at least one inhibitor of RP 105 and/or MD-I activity. Also disclosed are methods of identifying compounds that inhibit development of diet-induced obesity and/or one or more sequelae thereof. In some aspects, these methods comprise: providing at least one first cell comprising TLR4, MD-2. RP105. MD-K and a TLR4-responsive promoter operably linked to a nucleic acid sequence encoding a reporter, contacting the at least one first cell with lipopolysaccharide and with a candidate compound; and determining a level of expression of the reporter in the presence of the LPS and the candidate compound, in some aspects, these methods comprise: providing at least one first cell comprising TLR2, TLR1, TLR6, MD-2, RP H/S, MD-K and a TLR2-responsive promoter operably linked to a nucleic acid sequence encoding a reporter, contacting the at least one first cell with a lipopepude ligand of TLR2 and with a candidate compound, and determining a level of expression of the reporter in the presence of the lipopeptide ligand of TLR2 and the candidate compound.

1 Claim, 9 Drawing Sheets

METHODS OF TREATMENT AND PREVENTION OF DIET-INDUCED OBESITY AND SEQUELAE THEREOF

RELATED APPLICATIONS

The present application claims priority to U.S. Provisional Patent Application 60/964,084 filed Aug. 9, 2007. This application is incorporated herein by reference in its entirety.

REFERENCE TO GOVERNMENT SUPPORT

The invention was developed at least in part with the support of NIH grants R21 A1063183, R01 A1075159, and 5P30AR047363. The US government has certain rights in the invention.

REFERENCE TO SEQUENCE LISTING

A sequence listing, which is part of the present disclosure, includes a text file comprising nucleotide sequences. The sequence listing is incorporated herein by reference.

INTRODUCTION

Obesity is a primary risk factor for insulin resistance and type 2 diabetes mellitus (T2DM). It has become clear in recent years that inflammation provides a critical link between these two metabolic syndromes (obesity and T2DM) (Shoelson, S. E., et al., J. Chu. Invest. 116: 1793-1801, 2006). Previous work has suggested that toll-like receptor 4 (TLR4) plays a role in regulating both the development of obesity and its metabolic sequelae during high fat diets. One publication asserts that female TLR4-deficient mice (TLR4$^{-/-}$ mice) are protected from a high fat diet-induced insulin resistance, despite gaining increased weight on such diets, in comparison to wild type controls (Shi, H., et al., J. Clin. Invest 116: 3015-3025, 2006); a second publication asserts that male mice with a loss-of-function mutation in TLR4 are protected from diet-induced obesity and insulin resistance (Tsukomo, D. M. L., et al, Diabetes 56: 1986-1998, 2007). However both of these studies were conducted using non-isogenic strains of mice. In addition, while it has been thought that the relevant TLR4 ligands driving such inflammation in wild type mice are probably free fatty acids or oxidized lipopolysaccharide (LPS), a recent study has suggested that high fat diets lead to a sustained increase in endotoxemia that may provide the relevant TLR4 signal (Cani, P. D., et al., Diabetes 56: 1761-4767, 2007).

We recently discovered a novel endogenous inhibitor of Toll-like receptor-4 (TLR4) signaling in myeloid cells, RP105 (Divanovic, S., et al., Nature Immunol. 6: 571-578, 2005; International Patent Application Number WO 2005/110470; International Patent Application Number WO 2006/102408). RP105 (also referred to as CD180, Koarada, S., et al., Rheumatology 40: 1315-1321, 2001) is a physiological inhibitor of TLR4 signaling in vitro and in vivo, and is a TLR4 homolog. Further, like TLR4, whose association with a secreted protein, MD-2, is necessary for signaling, RP105 is dependent upon the MD-2 homolog, MD-1, for surface expression and function (Nagai, Y., et al., Blood 99, 1699-1705, 2002) Furthermore, we have shown that: (1) RP105 is a specific inhibitor of TLR4 signaling in HEK293 cells; (2) a complex comprising RP105 and MD-1 interacts directly with a complex comprising TLR4 and MD-2, wherein the RP105/MD-1 complex inhibits the ability of the TLR4/MD-2 complex to bind lipopolysaccharide (LPS); and (3) RP105 regulates in vivo responses to LPS. In addition, we have found that the phenotype of RP105-deficient mice are mirror images of those of reported for TLR4-deficient mice in other models, including Leishmania infection and bleomycin-induced lung toxicity (RP105-deficient mice being protected in both models).

US Patent Application 20040110146 to Dobie et al. discloses compounds, compositions and methods for modulating the expression of "MD-1. RP105 associated." However, this application does not: disclose methods of treating or preventing diet-induced obesity, or methods for identifying compounds effective for treating or preventing diet-induced obesity.

International Patent Application Number WO 00/12130 discloses methods of treating or preventing allergic diseases with RP105 antagonists, and methods of identifying RP105 antagonists. However, this application does not disclose methods of treating or preventing diet-induced obesity or sequelae thereof, nor does it disclose a method of identifying a compound which inhibits development of diet-induced Obesity or sequelae thereof.

SUMMARY

The present inventors have developed methods for treating and/or preventing diet-induced obesity and/or one or more sequelae thereof, as well as methods of screening candidate compounds which can be used to treat and/or prevent obesity and/or one or more sequelae thereof.

In various embodiments of the present teachings, methods developed by the inventors for treatment of diet-induced obesity and/or one or more sequelae thereof in a subject comprise administering to a subject in need of treatment a therapeutically effective amount of a pharmaceutical composition comprising at least one inhibitor of RP105 activity, at least one inhibitor of MD-1 activity, at least one inhibitor of RP105 expression, and/or at least one inhibitor of MD-1 expression. In other embodiments, the inventors disclose methods of preventing diet-induced obesity and/or one or more sequelae thereof in a subject. In various configurations, these methods can comprise administering to a subject at risk for developing diet-induced obesity and/or one or more sequelae thereof, a pharmaceutical composition comprising at least one inhibitor of RP105 activity, at least one inhibitor of MD-1 activity, at least one inhibitor of RP105 expression, and/or at least one inhibitor of MD-1 expression, in an amount effective for preventing, or facilitating prevention of development of diet-induced obesity and/or one or more sequelae thereof in a subject.

In various aspects of the present methods, an inhibitor of RP105 activity and/or MD-1 activity that can be used for treating or preventing diet-induced obesity and/or one or more sequelae thereof in a subject can be, without limitation, an antibody against RP105, an antibody against MD-1, an antibody against a complex comprising RP105 and MD-1 a peptide that blocks an interaction between a TLR2/MD-2 heterodimer and a RP105/MD-1 heterodimer, a peptide that blocks an interaction between TLR2 and a RP105/MD-1 heterodimer, or a peptide that blocks an interaction between TLR2 complexed with either TLR1 or TLR6 and a RP105/MD-1 heterodimer. In some configurations, an antibody can be any monoclonal antibody or a polyclonal antibody directed against RP105 and/or MD-1 known to skilled artisans, and can be generated using methods well known to skilled artisans.

In various other aspects of the present methods, an inhibitor of RP105 expression and/or MD-1 expression that can be used for treating or preventing diet-induced obesity and/or one or more sequelae thereof in a subject can be an interfering or inhibiting RNA which inhibits expression of RP105 and/or MD-1, such as, without limitation, an shRNA, an miRNA, an siRNA, and/or an anti-sense RNA. In some configurations, an interfering RNA or a precursor thereof can be one known to skilled artisans, such as a commercially available DNA encoding an shRNA or shRNA and having a sequence, in DNA form, such as CCTCTTGGTCTCCAGAGTCAG-GCATTCAA (SEQ ID NO: 1); CTACCTCAATCTGGCT-GCCAACAGCATTA (SEQ ID NO; 2); CATCAACCTAGC-CTGAACTTCAATGGCA (SEQ ID NO: 3); or GCAGGAACACCGCTTCTCTGACATCTCAT (SEQ ID NO: 4).

In some configurations, an inhibiting RNA can be an antisense RNA, such as, without limitation, an anti-sense RNA such as a phosphorothioated antisense oligonucleotide.

In various configurations of the present teachings, a sequela of diet-induced obesity which can be treated or prevented by the methods disclosed herein can be, without limitation, metabolic endotoxemia, insulin resistance, type 2 diabetes mellitus, glucose intolerance, inflammation, hepatic steatosis, steatohepatitis or a combination thereof. In some aspects, an inflammation can be, without limitation, liver inflammation, vascular inflammation, an inflammatory response in an adipose tissue, or a combination thereof.

In some embodiments of the present teachings, the inventors disclose methods of identifying a compound which inhibits development of diet-induced obesity and/or one or more sequelae thereof. In various configurations, a method of these embodiments can comprise: providing at least one first cell comprising TLR4, MD-2, RP105, and MD-1 proteins, and a TLR4-responsive promoter operably linked to a nucleic acid sequence encoding a reporter; contacting the at least one first cell with lipopolysaccharide (LPS) and with a candidate compound; and determining a level of expression of the reporter in the presence of the LPS and the candidate compound. In various configurations of these methods, detection of an elevated level of expression of the reporter in the presence of both the LPS and the candidate compound compared to the level of expression of the reporter in the presence of LPS but in the absence of the candidate compound indicates the compound inhibits development of diet-induced obesity and/or one or more sequelae thereof. Without being limited by theory, the inventors believe that a compound detected by this assay interferes with RP105/MD-1 inhibition of TLR4/MD-2 activity, and thereby inhibits development of diet-induced obesity and/or one or more sequelae thereof.

In various configurations, the at least one first cell of these embodiments can comprise DNA sequences encoding TLR4, MD-2, RP105, and MD-1 proteins, and a TLR4-responsive promoter operably linked to a nucleic acid sequence encoding a reporter. The sequences encoding TLR4, MD-2, RP105, and MD-1 proteins, and the nucleic acid comprising a TLR4-responsive promoter operably linked to a nucleic acid sequence encoding a reporter, can be endogenous to the cell, or can be exogenous sequences, such as sequences added by infection, transfection and/or transformation.

In some embodiments of the present teachings, the inventors disclose methods of identifying a compound which inhibits development of diet-induced obesity and/or one or more sequelae thereof. In various configurations, a method of these embodiments can comprise: providing at: least one first cell comprising TLR2, TLR1, TLR6, MD-2, RP105, and MD-1 proteins, and a TLR2-responsive promoter operably linked to a nucleic acid sequence encoding a reporter; contacting the at least one first cell with a lipopeptide ligand for TLR2 such as PAM3CYS and with a candidate compound; and determining a level of expression of the reporter in the presence of the lipopeptide ligand for TLR2 and the candidate compound. In various configurations of these methods, detection of an elevated level of expression of the reporter in the presence of both the lipopeptide ligand for TLR2 and the candidate compound compared to the level of expression of the reporter in the presence of the lipopeptide ligand for TLR2 but in the absence of the candidate compound indicates the compound inhibits development of diet-induced obesity and/or one or more sequelae thereof. Without being limited by theory, the inventors believe that a compound detected by this assay interferes with RP105/MD-1 inhibition of TLR2/MD-2 activity, and thereby inhibits development of diet-induced obesity and/or one or more sequelae thereof.

In various configurations, the at least one first cell of these embodiments can comprise DNA sequences encoding TLR2, TLR1, TLR6, MD-2, RP105, and MD-1 proteins, and a TLR2-responsive promoter operably linked to a nucleic acid sequence encoding a reporter. The sequences encoding TLR2, TLR1, TLR6, MD-2, RP105, and MD-1 proteins, and the nucleic acid comprising a TLR2-responsive promoter operably linked to a nucleic acid sequence encoding a reporter, can be endogenous to the cell, or can be exogenous sequences, such as sequences added by infection, transfection and/or transformation.

In various configurations, a cell comprising DNA sequences encoding a TLR4, an MD-2, an RP105, an MD-1, and a TLR4-responsive promoter operably linked to a nucleic acid sequence encoding a reporter can be a cell that is transiently transfected and/or a stably transfected with any or all of these DNA sequences. In various configurations, a cell of these embodiments can express and/or comprise TLR4, MD-2, RP105, MD-1 proteins. In various configurations, a cell comprising DNA sequences encoding a TLR2, a TLR1, a TLR6, an MD-2, an RP105, an MD-1, and a TLR2-responsive promoter operably linked to a nucleic acid sequence encoding a reporter can be a cell that is transiently transfected and/or a stably transfected with any or all of these DNA sequences. In various configurations, a cell of these embodiments can express and/or comprise TLR2, TLR1, TLR6, MD-2, RP105, MD-1 proteins. Under conditions appropriate for expression of a reporter under the control of a TLR4-responsive promoter or a TLR2-responsive promoter, a cell of these configurations can further express the reporter.

In various configurations of the present teachings, a TLR4-responsive promoter or a TLR2-responsive promoter can be any promoter known to skilled artisans that responds to an NF-κB induction signal, such as an NF-κB promoter. Furthermore, a reporter can be any polypeptide known to skilled artisans for which a signal can be detected directly or indirectly, and for which a nucleic acid sequence encoding the polypeptide is known. In various configurations, a reporter can be, without limitation, a polypeptide or protein for which a detection probe is available. A reporter and detection probe of these configurations can be, without limitation, a polypeptide for which an antibody is available, and the antibody; an enzyme which generates a detectable reaction product upon interacting with a substrate, such as a fluorogenic substrate, a chromogenic substrate, or a luminescent substrate. A reporter of these configurations can be, for example, an alkaline phosphatase or a luciferase such as a firefly luciferase. In some configurations, a reporter can be detected by virtue of its optical properties, such as, for example, a fluorescent protein such as a green fluorescent protein.

In various configurations of the present teachings, a cell comprising TLR4, MD-2, RP105, MD-1, and a TLR4-responsive promoter operably linked to a nucleic acid sequence encoding a reporter can be any type of vertebrate cell or mammalian cell, such as, without limitation, a primate cell. in various configurations of the present teachings, a cell comprising TLR2, TLR1, TLR6, MD-2, RP105, MD-1, and a TLR2-responsive promoter operably linked to a nucleic acid sequence encoding a reporter can be any type of vertebrate cell or mammalian cell, such as, without limitation, a primate cell. In various aspects, a mammalian cell can be a human cell and/or a kidney cell, such as, without limitation, a human embryonic kidney cell. In some aspects, a human embryonic kidney cell can be an HEK 293 cell.

In various configurations of the present teachings, a cell which can be used for identifying a compound which inhibits development of diet-induced obesity and/or one or more sequelae thereof can further comprise a second promoter-reporter construct, such as a DNA comprising a second promoter which drives expression of an operably linked second reporter at a level which does not vary in response to conditions that alter expression of a TLR4-responsive or TLR2-responsive promoter. Furthermore, a second reporter of these configurations can be a reporter that provides a signal that can be distinguished from that of a reporter that is expressed under the control of a TLR4-responsive or TLR2-responsive promoter. In some configurations, a second reporter can be, without limitation, a renilla luciferase. In some configurations, a promoter operably linked to a second reporter can be any reporter known to skilled artisans to support transcription at a level that is not modulated by NF-κB, such as, for example, a TK reporter.

In various embodiments of the present teachings, methods of identifying a compound which inhibits development of diet-induced obesity and/or one or more sequelae thereof can further include assays that test for elevation of cell responses to a test compound, in which a cell response does not require an interaction between an RP105/MD-1 complex and a TLR4/MD2 complex. In these embodiments. a method can further include: providing at least one second cell comprising TLR4, MD-2, and a TLR4-responsive promoter operably linked to a nucleic acid sequence encoding a reporter, wherein the at least one second cell does not comprise at least one of RP105 and MD-1; contacting the at least one second cell with LPS and with a candidate compound; and determining a level of expression of the reporter in the presence of the candidate compound. In these assays, an elevated level of expression in the at least one second cell of the reporter in the presence of LPS and the candidate compound in comparison to the level of expression of the reporter in the presence of LPS but in the absence of the candidate compound can indicate that the compound upregulates TLR4 signaling by a pathway independent of RP105 and/or MD-1.

In various configurations of the present teachings, a cell comprising TLR4, MD-2, and a TLR4-responsive promoter operably linked to a nucleic acid sequence encoding a reporter, but not comprising RP105 and/or MD-1, can be any type of vertebrate cell or mammalian cell, such as, without limitation, a primate cell. In various aspects, a mammalian cell of these configurations can be a human cell and/or a kidney cell, such as, without limitation, a human embryonic kidney cell. In some aspects, a human embryonic kidney cell can be an HEK 293 cell such as, without limitation, a human embryonic kidney cell such as a HEK 293 cell. In various aspects, the TLR4-responsive promoter operably linked to a nucleic acid sequence encoding a reporter can be an NF-κB promoter, and the reporter can be luciferase reporter.

In various embodiments of the present teachings, methods of identifying a compound which inhibits development of diet-induced obesity and/or one or more sequelae thereof can further include assays that test for elevation of cell responses to a test compound. in which a cell response does not require an interaction between an RP105/MD-1 complex and a TLR2/MD2 complex. In these embodiments, a method can further include: providing at least one second cell comprising TLR2, TLR1, TLR6, MD-2, and a TLR2-responsive promoter operably linked to a nucleic acid sequence encoding a reporter, wherein the at least one second cell does not comprise at least one of RP105 and MD-1; contacting the at least one second cell with a lipopeptide ligand of TLR2 and with a candidate compound; and determining a level of expression of the reporter in the presence of the candidate compound. In these assays. an elevated level of expression in the at least one second cell of the reporter in the presence of the lipopeptide ligand of TLR2 and the candidate compound in comparison to the level of expression of the reporter in the presence of the lipopeptide ligand of TLR2 but in the absence of the candidate compound can indicate that the compound upregulates TLR2 signaling by a pathway independent of RP105 and/or MD-1.

In various configurations of the present teachings, a cell comprising TLR2, TLR1, TLR6, MD-2, and a TLR2-responsive promoter operably linked to a nucleic acid sequence encoding a reporter, but not comprising RP105 and/or MD-1, can be any type of vertebrate cell or mammalian cell, such as, without limitation, a primate cell. In various aspects, a mammalian cell of these configurations can be a human cell and/or a kidney cell, such as, without limitation, a human embryonic kidney cell, in some aspects, a human embryonic kidney cell can be an HEK 293 cell such as, without limitation, a human. embryonic kidney cell such as a HEK 293 cell. In various aspects, the TLR2-responsive promoter operably linked to a nucleic acid sequence encoding a reporter can be an NF-κB promoter, and the reporter can be luciferase reporter.

In some embodiments of the present teachings, the inventors disclose methods of treating obesity and/or at least one sequela thereof. In various aspects, these methods comprise: selecting a compound identified by the methods set forth herein; and administering a therapeutically effective amount of a pharmaceutical composition comprising the compound to a subject in need of treatment.

In some embodiments of the present teachings, the inventors disclose methods of preventing obesity and/or at least one sequela thereof, the method comprising: selecting a compound identified by the methods set forth herein; and administering a pharmaceutical composition comprising the compound to a subject in an amount effective for preventing obesity and/or at least one sequela thereof.

In some embodiments of the present teachings, the inventors disclose use of a compound in the manufacture of a medicament for the treatment of obesity and/or one or more sequelae thereof. wherein the compound is selected from an antibody against RP105, an antibody against MD-1, an antibody against a complex comprising RP105 and MD-1, a peptide that blocks an interaction between RP105 and MD-1, a peptide that blocks an interaction between a TLR4/MD-2 heterodimer and a RP105/MD-1 heterodimer, a compound identified by the methods set forth herein, and an interfering or inhibiting RNA that inhibits expression of RP105 and/or MD-1.

In some configurations, an antibody which can be used in the manufacture of a medicament for the treatment of obesity and/or one or more sequelae thereof can be a monoclonal antibody or a polyclonal antibody, such as described herein. In addition, an interfering or inhibiting RNA which can be used in the manufacture of a medicament for the treatment: of obesity and/or one or more sequelae thereof can be an shRNA, an siRNA, an miRNA, or an antisense RNA.

DETAILED DESCRIPTION

Figure 1:
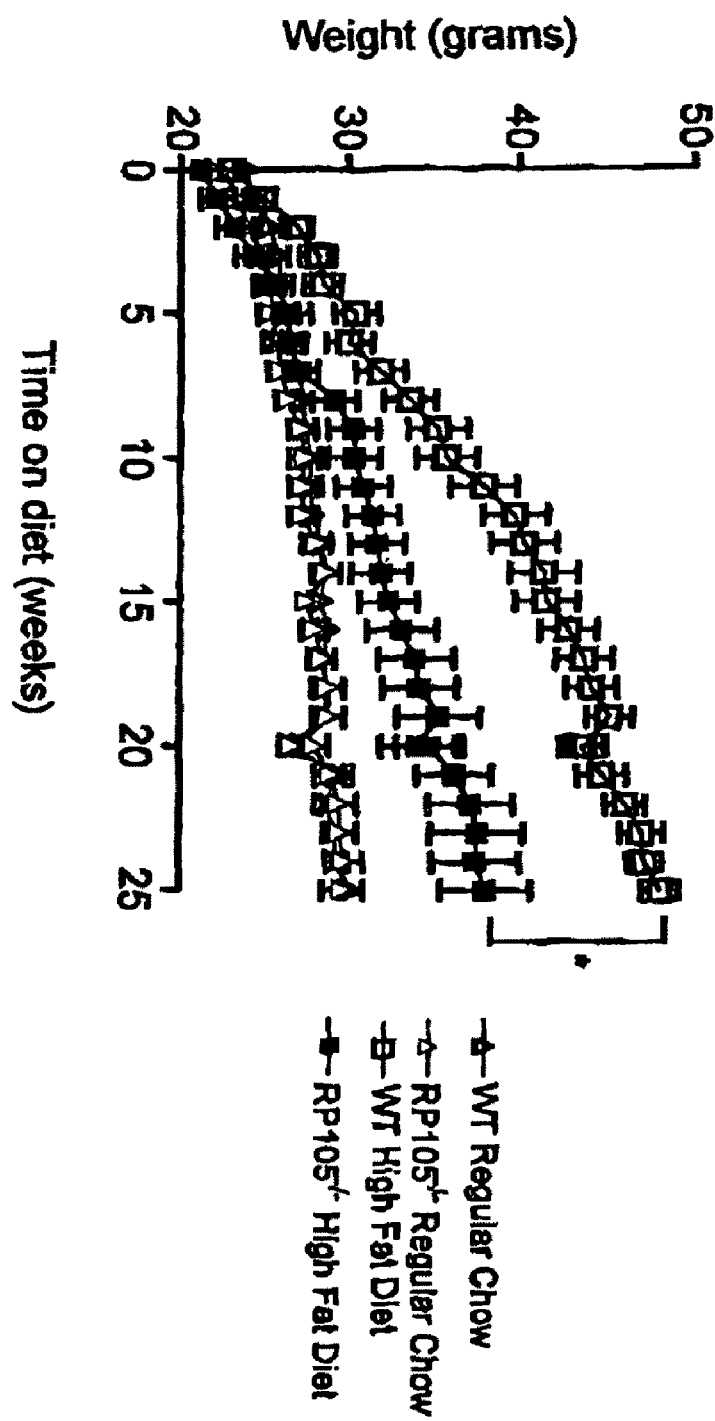
FIG. 1 illustrates that RP105-deficient mice show less weight gain compared to wild type mice fed a high fat diet.

Methods and compositions described herein utilize laboratory techniques well known to skilled artisans. Such techniques can be found in laboratory manuals such as Sambrook, J., et al. Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Harlow, E., Using Antibodies: A Laboratory Manual, Cold Spring Harbor Laboratory Press, Cold Spring Harbor, N.Y., 1999; and Sioud, M., ed. Ribozymes and siRNA Protocols, New York, Springer-Verlag, 2004; Sohail, M. ed., Gene Silencing by RNA Interference: Technology and Application, CRC Press LLC, Boca Raton, Fla., 2005; Schepers, U., RNA Interference in Practice: Principles, Basics, and Methods for Gene Silencing in *C. elegans, Drosophila*, and Mammals, Wiley-VCH Verlag GmbH & Co., Weinheim 2005; and Engelke, D., RNA Interference (RNAi) Nuts & Bolts of RNAi Technology, DNA Press LLC, 2003. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. As used in the description of the invention and the appended claims, the singular forms "a", "an" and "the" are intended to include the plural forms as well, unless the context indicates otherwise. All publications, patent applications, patents, and other references mentioned herein are incorporated by reference in each in its entirety.

The present inventors have found that when placed on a high fat diet (HFD), fully back-crossed C57BL/6 RP105$^{-/-}$ mice are: (a) protected from the development of obesity; (b) protected from the development of glucose intolerance, insulin resistance and type II diabetes; (c) protected from the development of hepatic steatosis; and (d) protected from the development of steatohepatitis; compared to wild type C57BL/6 mice. Furthermore, the inventors have found that fully back-crossed C57BL/6 TLR4$^{-/-}$ mice and C57BL/6 TLR2$^{-/-}$ mice have the opposite phenotype, developing: (a) increased obesity; (b) greater glucose intolerance, insulin resistance and exacerbated type II diabetes; (c) exacerbated hepatic steatosis; and (d) exacerbated steatohepatitis; compared to wild type C57BL/6 mice placed on a high fat diet.

Accordingly, the present inventors disclose, in various embodiments, methods for treating or preventing diet-induced obesity and/or one or more sequelae thereof in a subject. As used herein, a "subject" is an individual diagnosed with, suspected of having, or at risk of developing, diet-induced obesity and/or one or more sequelae thereof. In various configurations, methods of the present teachings can comprise administering to a subject in need of treatment of diet-induced obesity and/or one or more sequelae thereof, a therapeutically effective amount of a pharmaceutical composition comprising at least one inhibitor of RP105 activity, at least one inhibitor of MD-1 activity, at least one inhibitor of RP105 expression, and/or at least one inhibitor of MD-1 expression. Routine methods, well known to skilled artisans, can be used to diagnose diet-induced obesity and/or one or more sequelae thereof; to determine if a subject is at risk of developing diet-induced obesity and/or one or more sequelae thereof; and to determine dosage and administration route of a pharmaceutical comprising a compound described herein.

In some embodiments, the inventors disclose methods for preventing diet-induced obesity and/or one or more sequelae thereof in a subject. In various configurations, these methods can comprise administering to a subject at risk for developing diet-induced obesity and/or one or more sequelae thereof, a pharmaceutical composition comprising at least one inhibitor of RP105 activity, at least one inhibitor of MD-1 activity, at least one inhibitor of RP105 expression, and/or at least one inhibitor of MD-1 expression, in an amount effective for preventing, or facilitating prevention of, development of obesity and/or one or more sequelae thereof in a subject.

In various aspects of the present methods, an inhibitor of RP105 activity and/or MD-1 activity that can be used for treating or preventing diet-induced obesity and/or one or more sequelae thereof in a subject can be, without limitation, an antibody against RP105, an antibody against MD-1, an antibody against a complex comprising RP105 and MD-1, a peptide that blocks an interaction between RP105 and MD-1, or a peptide that blocks an interaction between a TLR4/MD-2 heterodimer and a RP105/MD-1 heterodimer. In some configurations, an antibody can be any monoclonal antibody or a polyclonal antibody known to skilled artisans that is directed against RP105, MD-1, or a complex comprising RP105 and MD-1. In some configurations, an antibody can be a commercially available antibody directed against RP105, such as, for example a rabbit polyclonal anti-human CD180 antibody such as supplied by Sigma-Aldrich Co., St. Louis, Mo.; Novus Biologicals, Inc., Littleton, Colo.; AnaSpec, Inc., San Jose, Calif.; RayBiotech, Inc., Norcross Ga.; a mouse monoclonal anti-human RP105 (CD180) antibody such as, for example, a monoclonal supplied by BioLegend, San Diego, Calif.; AbD Serotec, Raleigh, N.C.; LifeSpan Biosciences, Inc., Seattle, Wash.; Cell Sciences, Inc., Canton, Mass.; Novus Biologicals, Inc., Littleton, Colo.; Santa. Cruz Biotechnology, Inc., Santa. Cruz, Calif.; United States Biological, Swampscott, Mass.; MBL International Corp., Woburn, Mass.; and RayBiotech, Inc., Norcross Ga. In some configurations, an antibody can be a commercially available antibody directed against MD-1, such as, for example a rabbit polyclonal antibody against MD-1, such as supplied by ProSci, Inc., Poway, Calif.; a goat polyclonal antibody against MD-1, such as supplied by R & D Systems, Inc., Minneapolis, Minn.; or a mouse monoclonal antibody against MD-1, such as supplied by Santa Cruz Biotechnology, Inc., Santa Cruz, Calif. As used herein, the term "antibody" encompasses polyclonal and monoclonal antibodies, as well as fragments and derivatives of immunoglobulins that retain antigen binding properties. Non-limiting examples of antibodies include Fab fragments and F(ab')₂ fragments of immunoglobulins, as well as antibodies comprising a label such as a fluorophore, a radionuclide, or a hapten such as a biotin or a digoxygenin.

In various other aspects of the present methods, an inhibitor of RP105 expression and/or MD-1 expression that can be used for treating or preventing diet-induced obesity and/or one or more sequelae thereof in a subject can be an interfering or inhibiting RNA which inhibits expression of RP105 and/or MD-1, such as, without limitation, an shRNA, an miRNA, an siRNA, and/or an anti-sense RNA. An interfering RNA of these aspects can be an siRNA or a precursor thereof, such as an siRNA formed from digestion of an RP105 dsRNA or an MD-1 dsRNA with a Dicer enzyme, either within a cell or in vitro, using routine methods known to skilled artisans. In some configurations, an interfering RNA or a precursor thereof can be one known to skilled artisans, such as a commercially available DNA encoding an shRNA or siRNA that inhibits RP105 expression and has a sequence, in DNA form, such as CCTCTTGGTCTCCAGAGTCAGGCATTCAA (SEQ TD NO: 1); CTACCTCAATCTGGCTGCCAACAGCATTA (SEQ TD NO: 2); CATCAACCTAAGCCTGAACTTCAATGGCA (SEQ ID NO: 3); or GCAGGAACACCGCTTCTCGACATCTCAT (SEQ ID NO: 4). In some configurations, an interference RNA can be an siRNA supplied by a commercial manufacturer, such as an siRNA. against RP105 (CD180) (a HuSH™ 29mer shRNA) supplied by OriGene Technologies, Inc., Rockville, Md.

In some configurations, an interfering RNA can be an antisense RNA, such as, without limitation, a phosphorothioated antisense oligonucleotide. In non-limiting example, antisense RNA targeted to three regions within the coding sequence of the murine MD-1 RP105-associated mRNA can inhibit of LPS-induced up-regulation of cell surface CD80/CD86 (Gorczynski et al., J. Immunol., 2000, 165, 1925-1932).

An interference RNA which can be used to treat or prevent diet-induced obesity and/or one or more sequelae thereof in a subject can be selected or generated using standard procedures well known to skilled artisans, based upon a known sequence of an RP105 cDNA, such as the sequence assigned accession number NM_005582 and having the sequence set forth below:

```
(SEQ. ID NO: 5)
agaatgctgagcagtcaacagcatttcttgttccaagatcacccttctgagtacctctctggctgccaaattgccagggccttcacagtttg attccatttctcagctccaagcattaggtaaacccaccaagcaatcctagcctgtgatggcgtttgacgtcagctgcttcttttgggtggtg ctgttttctgccggctgtaaagtcatcacctcctgggatcagatgtgcattgagaaagaagccaacaaaacatataactgtgaaaatttag gtctcagtgaaatccctgacactctaccaaacacaacagaattttttggaattcagctttaattttttgcctacaattcacaatagaaccttcag cagactcatgaatcttaccttttttggatttaactaggtgccagattaactggatacatgaagacacttttcaaagccatcatcaattaagcac acttgtgttaactggaaatcccctgatattcatggcagaaacatcgcttaatgggcccaagtcactgaagcatcttttcttaatccaaacgg gaatatccaatctcgagtttatttccagtgcacaatctggaaaacttggaaagcttgtatcttggaagcaaccatatttcctccattaagttcc ccaaagacttcccagcacggaatctgaaagtactggattttcagaataatgctatacactacatctctagagaagacatgaggtctcygg agcaggccatcaacctaagcctgaacttcaatggcaataatgttaaaggtattgagcttggggcttttgattcaacgatcttccaaagtttg aactttggaggaactccaaatttgtctgttatattcaatggtctgcagaactctactactcagtctctctggctgggaacatttgaggacatt gatgacgaagatattagttcagccatgctcaagggactctgtgaaatgtctgttgagagcctcaacctgcaggaacaccgcttctctgac atctcatccaccacatttcagtgcttcacccaactccaagaattggatctgacagcaactcacttgaaagggttaccctctgggatgaag ggtctgaacttgctcaagaaattagttctcagtgtaaatcatttcgatcaattgtgtcaaatcagtgctgccaatttcccctccttacacacc tctacatcagaggcaacgtgaagaaacttcaccttggtgttggctgcttggagaaactaggaaaccttcagacacttgatttaagccata atgacatagaggcttctgactgctgcagtctgcaactcaaaaacctgtcccacttgcaaaccttaaacctgagccacaatgagcctcttgg gtctccagagtcaggcattcaaagaatgtcctcagctagaactcctcgatttggcatttacccgcttacacattaatgctccacaaagtcc cttccaaaacctccatttccttcaggttctgaatctcacttactgcttcttgataccagcaatcagcatcttctagcaggcctaccagttctc cggcatctcaacttaaaagggaatcactttcaagatgggactatcacgaagaccaacctacttcagaccgtgggcagcttggaggttct gattttgtcctcttgtggtctcctctatagaccagcaagcattccacagcttgggaaaaatgagccatgtagacttaagccacaacagc ctgacatgcgacagcattgattctcttagccatcttaagggaatctacctcaatctggctgccaacagcattaacatcatcacccccgtct cctccctatcttgtcccagcagagcaccattaatttaagtcataaccccctggactgcacttgctcgaatattcatttcttaactggtacaa
```

-continued
```
agaaaacctgcacaaacttgaaggctcggaggagaccacgtgtgcaaacccgccatctctaaggggagttaagctatctgatgtcaa gctttcctgtgggattacagccataggcattttctttctcatagtatttctattattgttggctattctgctattttttgcagttaaataccttctcag gtggaaataccaacacatttagtgctgaaggtttccagagaaagcaaataagtgtgcttagcaaaattgctctaagtgaaagaactgtca tctgctggtgaccagaccagactttcagattgttcctggaactgggcagggactcactgtgcttttctgagcttcttactcctgtgagtcc cagagctaaagaaccttctaggcaagtacaccgaatgactcagtccagagggtcagatgctgctgtgagaggcacagagcctttcc gcatgtggaagagtgggaggaagcagagggagggactgggcagggactgccggcccggagtctcccacagggaggccattcc ccttctactcaccgacatccctcccagcaccacacacccgccctgaaaggagatcatcagcccccacaatttgtcagagctgaagc cagcccactacccaccccactacagcattgtgctgggtctgggttctcagtaatgtagccatttgagaaacttacttggggacaaagt ctcaatccttattttaaatgaaaaagaaaagaaaagcataataaatttaaaagaaaaggctgagaaatgaaaaaaaaaaaa.
```

An interference RNA which can be used to treat or prevent diet-induced obesity and/or one or more sequelae thereof in a subject can be selected by generating an siRNA using standard procedures and protocols well known to skilled artisans, based upon a known sequence of an MD-1 cDNA, such as the sequence assigned accession number BC038846 and having the sequence set forth below:

(SEQ ID NO: 6)
```
ccacgcgtccgtgttttctgtgtgtcccatacaggcccccaccatgaagggtttcacagccactctcttcctctggactgattttcccca gctgcagtggaggcggcggtgggaaagcctggcccacacacgtggtctgtagcgacagcggcttggaagtgctctaccagagttgc gatccattacaagattttggcttttctgttgaaaagtgttccaagcaattaaaatcaaatatcaacattagatttggaattattctgagagagg acatcaaagagcttttcttgacctagctctcatgtctcaaggctcatctgttttgaatttctcctatcccatctggtgaggcggctctgcccaa gttttctttctgtggaagaaggaaaggagagcagatttactatgctgggcctgtcaataatcctgaatttactattcctcagggagaatacc agggttttgctggaactgtacactgaaaaacggtccaccgtggcctgtgccaatgctactatcatgtgctccgtgactgtggcctgtagcaa aaatcacagccagctgcatctcgtgggacctccaagctcctctgactgaacctactgtgggaggagaagcagctgatgacagagaga ggctctacaaagaagcgcccccaaagagtgcagctgctaattttagtcccaggaccagacatccccagactccacagatgtaatgaa gtcccgaatgtatctgtttctaaggagcctcttggcagtccttaagcagtcttgagggtccatccttttttctcaattggtcgcctcccacc agactcacctgcttttcaactttttaggagtgcttcctcacagttaccaagaataaagaaagctggccaccataaaaaaaaaaaaaaaa.
```

In various configurations of the present teachings, a skilled artisan, such as a medical doctor, can diagnose diet-induced obesity and/or various sequelae thereof by well known methods. In various configurations non-limiting examples of sequelae of diet-induced obesity which can be treated or prevented by the methods disclosed herein can include, without limitation, metabolic endotoxemia, insulin resistance, type 2 diabetes mellitus, glucose intolerance, inflammation, hepatic steatosis, steatohepatitis or a combination thereof. In some aspects, examples of an inflammation can include, without limitation, a liver inflammation, a vascular inflammation, an inflammatory response in an adipose tissue, or a combination thereof.

In some embodiments of the present teachings, the inventors disclose methods of identifying a compound which inhibits development of diet-induced obesity and/or one or more sequelae thereof in various configurations, a method of these embodiments can comprise: providing at least one first cell comprising TLR4, MD-2, RP105, MD-1, and a TLR4-responsive promoter operably linked to a nucleic acid sequence encoding a reporter; contacting the at least one first cell with lipopolysaccharide (LPS) and with a candidate compound; and determining a level of expression of the reporter in the presence of the LPS and the candidate compound. In various configurations of these methods, detection of an elevated level of expression of the reporter in the presence of both the LPS and the candidate compound compared to the level of expression of the reporter in the presence of LPS but in the absence of the candidate compound indicates that the compound inhibits development of diet-induced obesity and/or one or more sequelae thereof. Without being limited by theory, the inventors believe that a compound detected by this assay interferes with RP105/MD-1 inhibition of TLR4/MD-2 activity, and thereby inhibits development of diet-induced obesity and/or one or more sequelae thereof. Compounds that can be tested for diet-induced obesity prevention or diet-induced obesity treatment using an assay of the present teachings can be any organic and/or biological compound, such as a compound which can be obtained from a commercial supplier or synthesized in a laboratory. In various aspects, the present assay lends itself to multiplex and/or high throughput screening assays, in which, for example, one or more multi-well plates (such as 384-well plates) are provided, in which a plurality of wells comprise cells comprising TLR4, MD-2, RP105, MD-1, and a TLR4-responsive promoter operably linked to a nucleic acid sequence encoding a reporter. Both lipopolysaccharide (LPS) and various candidate compounds can be applied to individual wells. In various configurations, the LPS and a candidate compound can be mixed prior to application of the mixture to cells; the LAS can be applied to cells prior to application of a candidate compound; or a candidate compound can be applied to cells prior to application of LPS. After application of LPS and a candidate compound, expression level of the reporter can then be measured for each well, and compared to expression level of the reporter in wells receiving LPS but not a candidate compound. For each well, an elevated level of expression of the reporter in the presence of LPS and a candidate compound compared to the level of expression of the reporter in the presence of LPS but in the absence of the candidate compound indicates that the compound can inhibit or prevent development of diet-induced obesity and/or one or more sequelae thereof. These assays can also be used to identify compounds that interfere with RP105/MD-1 inhibition of TLR4/MD-2 activity, and thereby can be useful for identifying compounds useful for treating and/or preventing diet-induced obesity and/or one or more sequelae thereof in a subject.

In some configurations, a reporter gene operably linked to a TLR4-responsive promoter can encode a protein or polypeptide which can be detected in a high throughput assay. For example, the reporter can be, without limitation, a fluorescent protein such as a green fluorescent protein, or a luciferase, such as a firefly luciferase. When a fluorescent protein is used as a reporter, fluorescence or bioluminescence can be detected in wells of an assay by direct observation by a human or by an automated light detection system, such as, for example, a PlateTrak™ high throughput screening (HTS) platform supplied by CCS Packard, Inc., Meriden, Conn. In such a system, quantitative comparison of light emission intensities from wells comprising cells, LPS, and candidate compounds (or a control) can be used to identify compounds. In addition In various configurations, the at least one first cell of these embodiments can comprise DNA segments encoding TLR4, MD-2, RP105, and MD-1 proteins. In various configurations, each DNA segment can be under the control of an operably linked promoter. Furthermore, the at least one first cell can comprise a DNA segment comprising a TLR4-responsive promoter operably linked to a nucleic acid sequence encoding a reporter. The sequences encoding TLR4, MD-2, RP105, MD-1, and the nucleic acid comprising a TLR4-responsive promoter operably linked to a nucleic acid sequence encoding a reporter can be endogenous to the cell, or can be exogenous sequences, such as sequences added by transfection and/or transformation. In various configurations, the DNA segments can each be comprised by a vector such as a virus or a plasmid. In some configurations, a single vector can comprise DNA sequences encoding one, two or more of TLR4, MD-2, RP105, and MD-1.

In various configurations, a cell comprising DNA sequences encoding a TLR4, an MD-2, an RP105, an MD-1, and a TLR4-responsive promoter operably linked to a nucleic acid sequence encoding a reporter can be a cell that is transiently transfected and/or a stably transfected with any or all of these DNA sequences. In various configurations, a cell of these embodiments can express and comprise TLR4, MD-2, RP105, MD-1 proteins. Under conditions that promote expression of a reporter, a cell of these configurations can further express the reporter.

In various configurations of the present teachings, a TLR4-responsive promoter can be any promoter known to skilled artisans that responds to TLR4 induction signal, such as an NF-κB promoter (Ohnishi, T., et al., J. Immunol 167: 3354-3359, 2001). Furthermore, a reporter can be any polypeptide known to skilled artisans for which a signal can be detected directly or indirectly, and for which a nucleic acid sequence encoding the polypeptide is known. In various configurations, a reporter can be, without limitation, a polypeptide or protein for which a detection probe is available, such as an antibody against the polypeptide or protein; an enzyme for which a substrate is available that can be used for detecting or assaying enzyme activity, such as, for example, a peroxidase, an alkaline phosphatase, or luciferase such as a firefly luciferase; or a polypeptide or protein that can be detected by virtue of its optical properties, such as, for example, a fluorescent protein such as a green fluorescent protein.

In various configurations of the present teachings, a cell comprising TLR4, MD-2, RP105, MD-1, and a TLR4-responsive promoter operably linked to a nucleic acid sequence encoding a reporter can be any type of vertebrate cell or mammalian cell, such as, without limitation, a primate cell. In various aspects, a mammalian cell can be a human cell and/or a kidney cell, such as, without limitation, a human embryonic kidney cell. In some aspects, human embryonic kidney cells that can be used in the various embodiments of the present teachings can be HEK 293 cells, available from American Type Culture Collection, Manassas, Va.

In various configurations of the present teachings, a cell which can be used for identifying a compound which inhibits development of diet-induced obesity and/or one or more sequelae thereof can thither comprise a second promoter-reporter construct, such as a DNA comprising a second promoter which drives expression of an operably linked second reporter at a level which does not vary in response to conditions that alter expression of a TLR4-responsive promoter. Furthermore, a second reporter of these configurations can be a reporter that provides a signal that can be distinguished from that of a reporter that is expressed under the control of a TLR4-responsive promoter. In some configurations, a second reporter can be, without limitation, a renilla luciferase. In some configurations, a promoter operably linked to a second reporter can be any reporter known to skilled artisans that supports transcription at a level that is not modulated by NF-κB, such as, for example, a TK reporter.

In various embodiments of the present teachings, methods of identifying a compound which inhibits development of diet-induced obesity and/or one or more sequelae thereof can further include assays that test for elevation of cell responses to a test compound, in which a cell response does not require an interaction. between an RP105/MD-1 complex and a TLR4/MD2 complex. In these embodiments, a method can further include: providing at least one second cell comprising TLR4, MD-2, and a TLR4-responsive promoter operably linked to a nucleic acid sequence encoding a reporter, wherein the at least one second cell does not comprise at least one of RP105 and MD-1; contacting the at least one second cell with LPS and with a candidate compound; and determining a level of expression of the reporter in the presence of the candidate compound. In these assays, an elevated level of expression of the reporter in the at least one second. cell in the presence of LPS and the candidate compound in comparison to the level of expression of the reporter in the presence of LPS but in the absence of the candidate compound can indicate that the compound upregulates TLR4 signaling by a pathway independent of RP105 and/or MD-1.

In various configurations of the present teachings, a cell comprising TLR4, MD-2, and a TLR4-responsive promoter operably linked to a nucleic acid sequence encoding a reporter, but not comprising RP105 and/or MD-1, can be any type of vertebrate cell or mammalian cell, such as, without limitation, a primate cell. In various aspects, a mammalian cell of these configurations can be a human cell and/or a kidney cell, such as, without limitation, a human embryonic kidney cell. In some aspects, a human embryonic kidney cell can be an HEK cell such as, without limitation, a human embryonic kidney cell such as a HEK cell. In various aspects, the TLR4-responsive promoter operably linked to a nucleic acid sequence encoding a reporter can be an NF-κB promoter, and the reporter can be luciferase reporter.

In some configurations, the at least one second cell can be a cell of the same cell type as the at least one first cell. In some configurations, without limitation, cells comprising DNA sequences encoding a TLR4, an MD-2, an RP105, an MD-1, and a TLR4-responsive promoter operably linked to a nucleic acid sequence encoding a reporter, and cells comprising TLR4, MD-2, and a TLR4-responsive promoter operably linked to a nucleic acid sequence encoding a reporter, but not comprising RP105 and/or MD-1, can both be human embryonic kidney HEK293 cells.

In some configurations, a high-throughput screening system for identifying a compound that inhibits development of diet-induced obesity and/or one or more sequelae thereof, can include not only assays for expression of a reporter under the control of a TLR4-responsive promoter in a cell comprising TLR4, MD-2, RP105 and MD-1, it can also include assays for expression of a reporter under the control of a TLR4-responsive promoter in a cell comprising TLR4 and MD-2, but not at least one of RP105 and MD-1. In some configurations, the two assays can be performed sequentially or simultaneously. In a non-limiting example, an initial screen using cells comprising TLR4 and MD-2, but not at least one of RP105 and MD-1, can be used to identify compounds that do not cause a signal increase. Compounds identified in this initial screen can then be tested on cells comprising TLR4, MD-2, RP105 and MD-1. Those compounds that do not cause a signal increase in cells comprising TLR4 and MD-2 but not at least one of RP105 and MD-1, but do cause a signal increase in cells comprising TLR4, MD-2, RP105 and MD-1, can be compounds that have potential pharmacological utility for treating and/or preventing diet-induced obesity and/or one or more sequelae thereof.

In some embodiments of the present teachings, the inventors disclose methods of treating obesity and/or at least one sequela thereof. in various aspects, these methods comprise: selecting a compound identified by the methods set forth herein; and administering a therapeutically effective amount of a pharmaceutical composition comprising the compound to a subject in need of treatment.

In some embodiments of the present teachings, the inventors disclose methods of preventing obesity and/or at least one sequela thereof, the method comprising: selecting a compound identified by the methods set forth herein; and administering a pharmaceutical composition comprising the compound to a subject in an amount effective for preventing obesity and/or at least one sequela thereof.

In some embodiments of the present teachings, the inventors disclose uses of a compound in the manufacture of a medicament for the treatment of obesity and/or one or more sequelae thereof wherein the compound is selected from an antibody against RP105, an antibody against MD-1, an antibody against a complex comprising RP105 and MD-1, a peptide that blocks an interaction between RP105 and MD-1, an interfering RNA, and a peptide that blocks an interaction between a TLR4/MD-2 heterodimer and a RP105/MD-1 heterodimer, and a compound identified by the methods set forth herein.

In some configurations, an antibody which can be used in the manufacture of a medicament for the treatment of obesity and/or one or more sequelae thereof can be a monoclonal antibody or a polyclonal antibody, such as described herein. In addition, an interfering RNA which can be used in the manufacture of a medicament for the treatment of obesity and/or one or more sequelae thereof can be an shRNA, an siRNA, an miRNA, or an antisense RNA.

EXAMPLES

The following examples illustrate various embodiments, aspects and configurations of the present teachings. These examples are not intended to limit the scope of any claim.

Example 1

This example illustrates that RP105-deficient mice show comparatively less weight gain than wild type mice fell a high fat diet.

In these experiments, RP105-deficient mice (RP105$^{-/-}$ mice), previously described in Ogata, H., et al., J. Exp. Med. 192, 23-30, 2000 and Divanovic, S., et al., Nature immunology 6: 571-578, 2005 were supplied by Dr. Alexander Tarakhovsky of The Rockefeller University and maintained by standard procedures. These mice were backcrossed for more than 11 generations to a C57BL/6 background and are considered fully back-crossed. Populations of control wild type (WT) and RP105-deficient mice were placed on either a regular chow diet (n=6 of each genotype) or on a high fat diet (n=10 of each genotype), beginning at 8 weeks of age. As shown in FIG. 1, WT mice fed a high fat diet steadily increased in weight, and reached almost 50 grams by 25 weeks. However, RP105-deficient mice fed a high fat diet only reached approx. 38 grams. In contrast, both WT and RP105-deficient mice fed a regular diet did not exceed a weight of about 30 grams after 25 weeks. These data demonstrate that RP105-deficient mice exhibit significantly less weight gain compared to WT mice on a high fat diet, and imply that inhibition of RP105 activity can prevent development of diet-induced obesity.

Example 2

This example illustrates that in comparison to wild type mice fed a high fat diet, RP105-deficient mice fed a high fat diet show less weight gain, although TLR4-deficient and TLR2-deficient mice fed a high fat diet show more weight gain.

Figure 2:
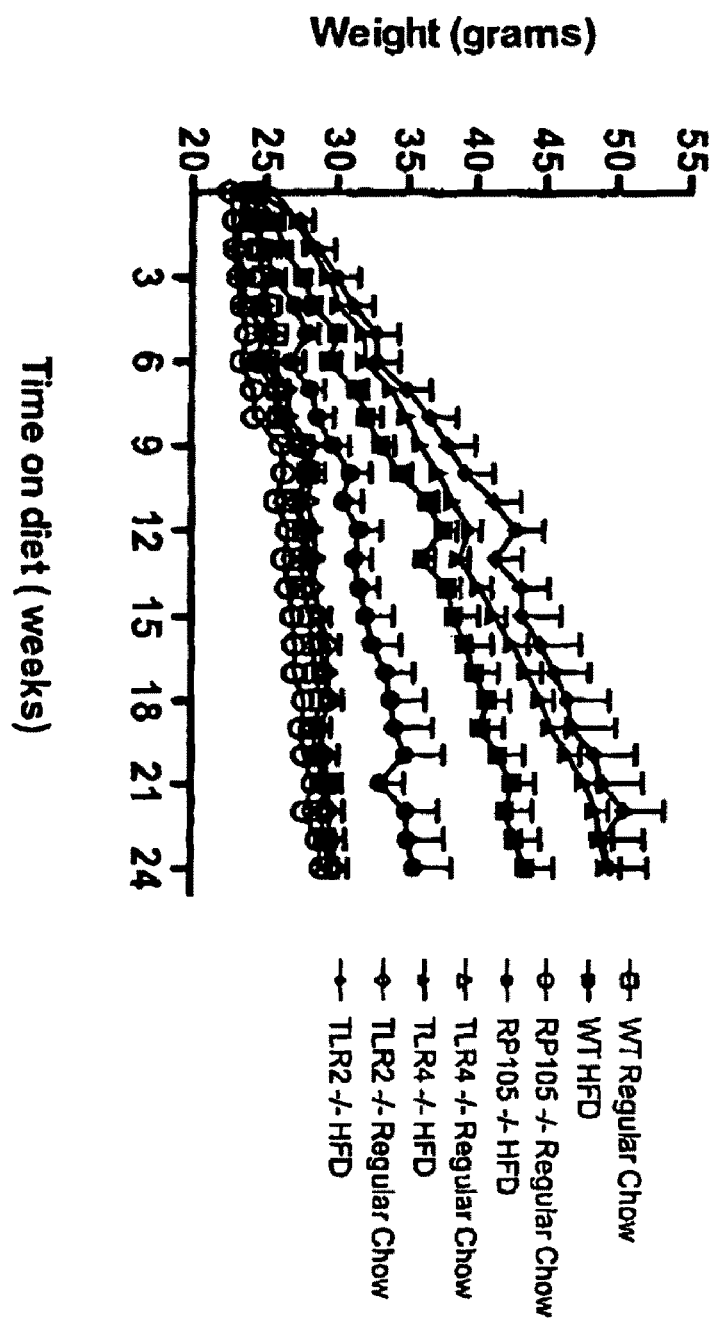
FIG. 2 illustrates that RP105-deficient mice show less weight gain compared to wild type mice fed a high fat diet, and that, in contrast, TLR4-deficient and TLR2-deficient mice show more weight gain compared to wild type mice fed a high fat diet.
Figure 3:
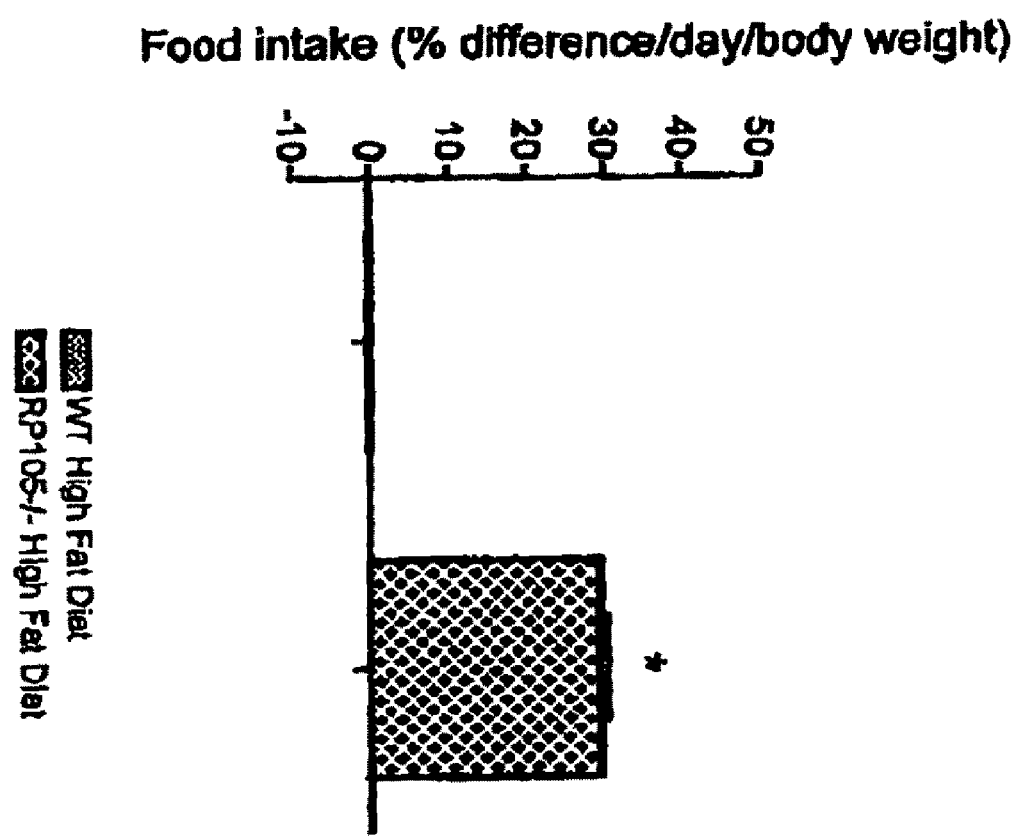
FIG. 3 illustrates increased daily high fat food intake in RP105-deficient mice compared to wild type mice.

In these experiments, fully back-crossed mice deficient for RP105, TLR4, or TLR2, as well as wild type mice, were fed either a high fat diet or a regular diet and animal weights were measured over the course of 25 weeks, as described in Example 1. As shown in FIG. 2, when comparisons are made between fully back-crossed genetically deficient mice and wild type mice, RP105-deficient mice fed a high fat diet exhibit comparatively less weight gain, while TLR4-deficient and TLR2-deficient mice actually exhibit comparatively greater weight gain.

Example 3

This example illustrates that RP105-deficient mice have increased daily food intake while on a high fat diet, compared to wild type mice.

In these experiments, wild type and RP105-deficient mice were fed a high fat diet, as described in Example 1. As shown in FIG. 2, the RP105-deficient mice showed significantly greater food intake compared to the wild type mice, although as was shown in Example 1, the wild type mice exhibited greater weight gain compared to the RP105-deficient mice.

Example 4

This example illustrates increased daily high fat food intake in RP105-deficient mice compared to wild type, TLR4-deficient and TLR2-deficient mice.

Figure 4:
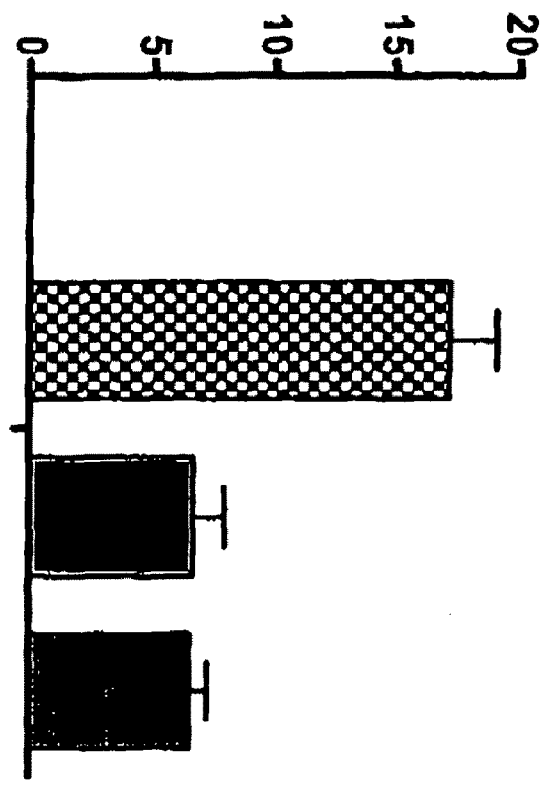
FIG. 4 illustrates increased daily high fat food intake in RP105-deficient mice compared to wild type, TLR4-deficient and TLR2-deficient mica.

In these experiments, fully back-crossed mice deficient for RP105, TLR4, or TLR2, as well as wild type mice, were fed a high fat diet as described above, and food intake was monitored. As shown in FIG. 4, RP105-deficient mice had significantly greater increase in food intake, in comparison to wild type mice as well as to TLR4-deficient and TLR2-deficient mice.

Example 5

This example illustrates that RP105-deficient mice develop less adiposity compared to wild type mice.

Figure 5:
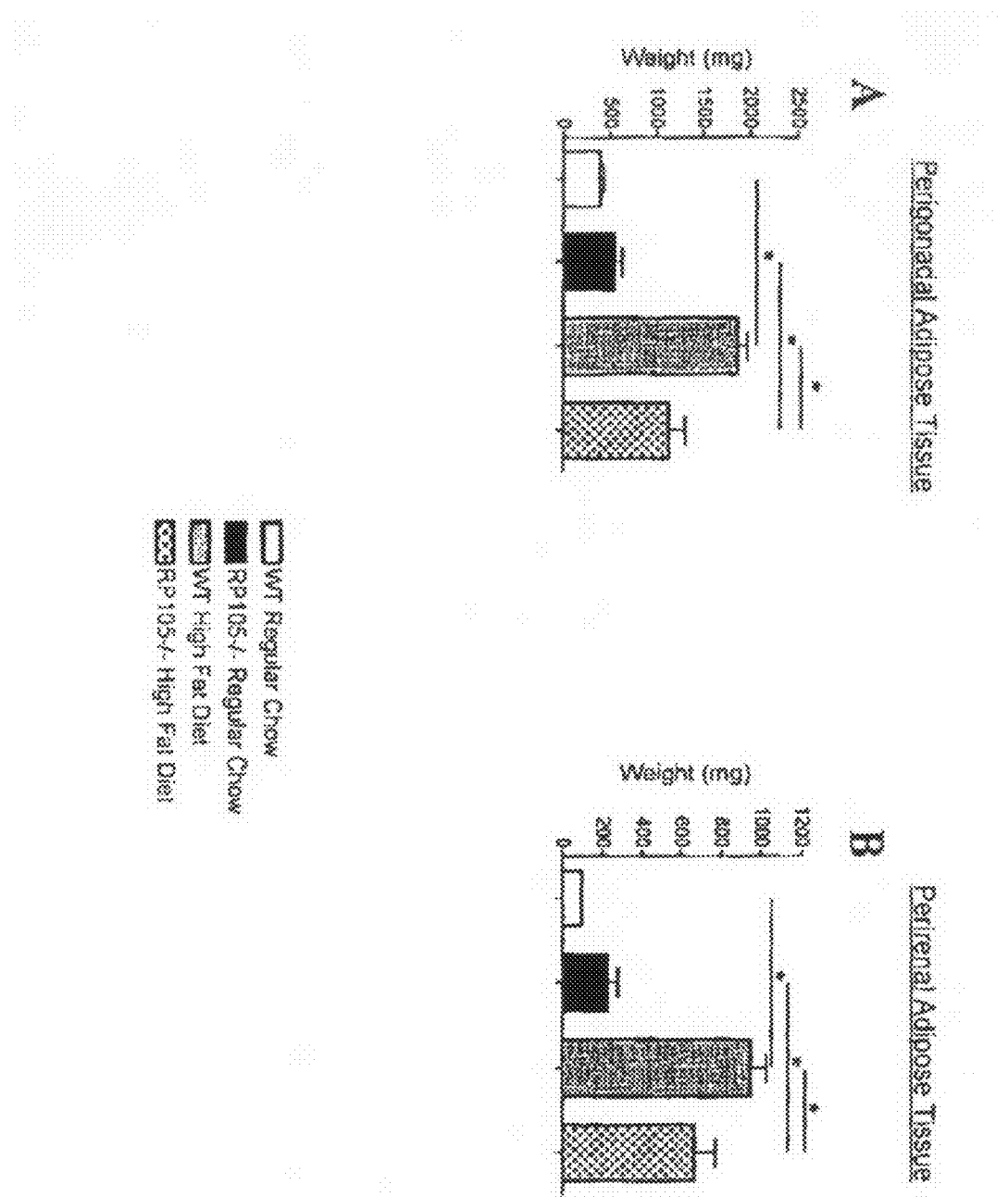
FIG. 5 illustrates that RP105-deficient mice develop less adiposity on a high fat diet compared to wild type mice.

In these experiments, wild type and fully backcrossed RP105-deficient mice were fed either a regular chow diet or a high fat diet, as described in Example 1. Various adipose tissues were weighed after 25 weeks. As shown in FIG. 5, wild type mice fed a high fat diet showed much. greater weight gain in perigonadal adipose tissue and perirenal adipose tissue compared to RP105-deficient mice (FIG. 5A and FIG. 5B).

These data demonstrate that RP105-deficient mice exhibit significantly less weight gain in adipose tissue compared to WT mice when both are kept on a high fat diet, and imply that inhibition of RP105 activity can reduce the development of adiposity (FIG. 5C).

Example 6

This example illustrates protection from glucose intolerance and insulin resistance in RP105-deficient mice.

Figure 6:
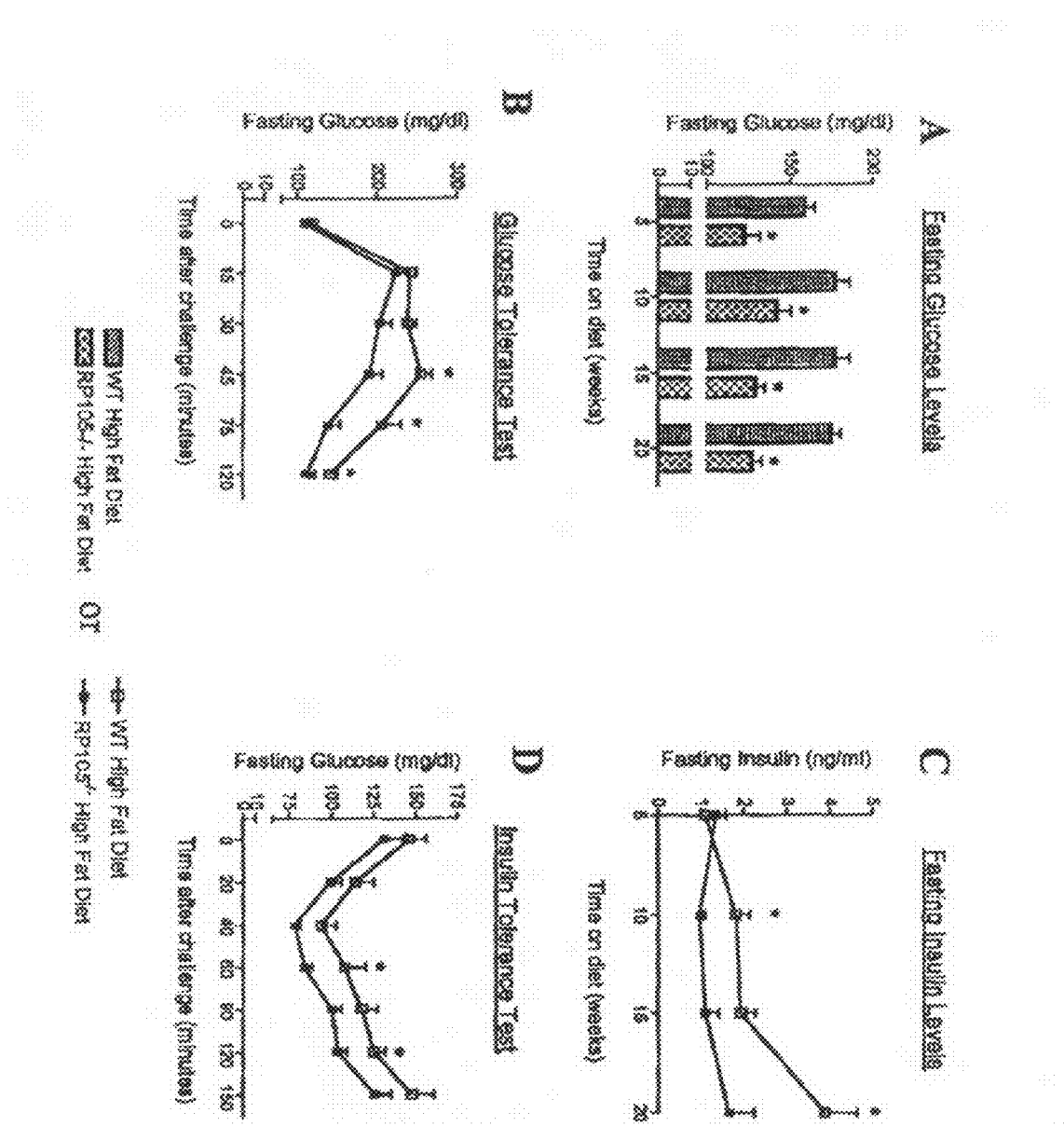
FIG. 6 illustrates protection from high fat diet-related glucose intolerance and insulin resistance in RP105-deficient mice.

In these experiments, wild type and fully back-crossed RP105-deficient mice as described in Example 1 were tested for fasting glucose levels, glucose tolerance, fasting insulin levels, and insulin tolerance. As shown in FIG. 6A, RP105-deficient mice fed a high fat diet showed significantly lower glucose levels compared to wild type mice fed a high fat diet; at all time points tested (5, 10, 15, and 20 weeks). In a glucose tolerance test, RP105-deficient mice fed a high fat diet showed significantly lower glucose levels compared to WT mice fed a high fat diet during the 120 minute duration of the test (FIG. 6B). In addition, in a measurement of fasting insulin levels, RP105-deficient mice showed significantly lower fasting glucose levels compared to WT mice during the interval from 10 to 20 weeks on a high fat diet (FIG. 6C). Furthermore, in an insulin tolerance test, RP105-deficient mice fed a high fat diet showed lower fasting glucose levels compared to WT mice fed a high. fat diet during the 150 minute duration of the test (FIG. 6D).

These data thus demonstrate that RP105-deficient mice exhibit protection from glucose intolerance and insulin resistance, and imply that inhibition of RP105 activity can provide protection from glucose intolerance and insulin resistance.

Example 7

This example illustrates protection from glucose intolerance and insulin resistance in RP105-deficient mice, exacerbated glucose intolerance and insulin sensitivity in TLR4-deficient and TLR2-deficient mice, compared to wild type mice.

Figure 7:
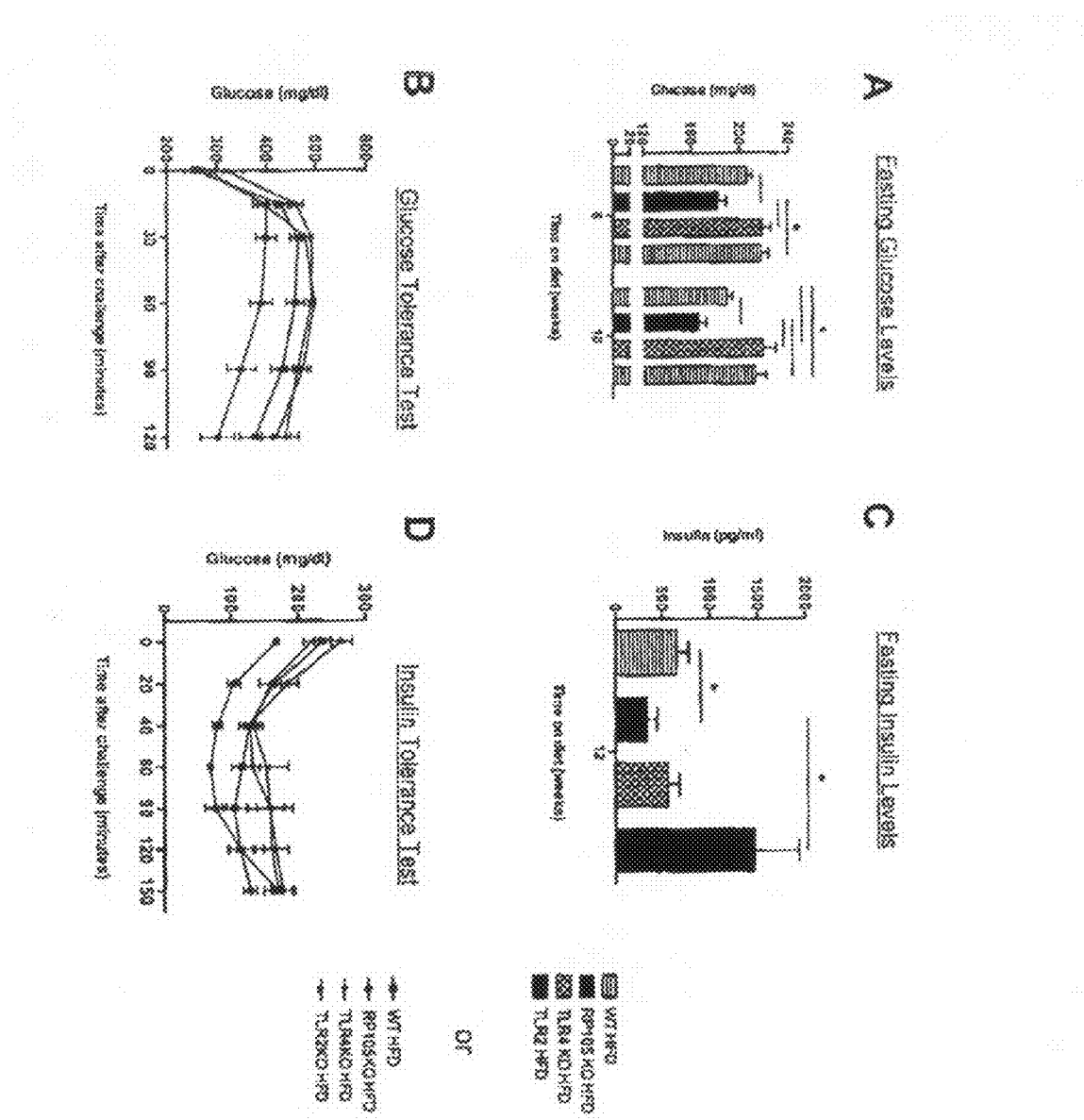
FIG. 7 illustrates protection from high fat diet-related glucose intolerance and insulin resistance in RP105-deficient mice, and exacerbation of high fat diet-related glucose intolerance and insulin sensitivity in TLR4-deficient and TLR2-deficient mice, compared with wild type mice.

In these experiments fully back-crossed mice deficient for RP105, TLR4, or TLR2, as well as wild type mice, were fed a high fat diet as described above, and were tested for fasting glucose levels, glucose tolerance, fasting insulin levels, and insulin tolerance. As shown in FIG. 7A, RP105-deficient mice fed a high fat diet showed significantly lower glucose levels compared to wild type mice, TLR4-deficient mice, or TLR2-deficient mice fed a high fat diet, at the time points tested (5 and 10 weeks). In a glucose tolerance test, RP105-deficient mice fed a high fat diet showed significantly lower glucose levels compared to WT mice, TLR4-deficient mice, or TLR2-deficient mice fed a high fat diet during the 120 minute duration of the test (FIG. 7B). In addition, in a measurement of fasting insulin levels, RP105-deficient mice showed significantly lower fasting glucose levels compared to WT mice, TLR4-deficient mice, or TLR2-deficient mice at 12 weeks on a high fat diet (FIG. 7C). Furthermore, in an insulin tolerance test, RP105-deficient mice fed a high fat diet showed lower fasting glucose levels compared to WT mice, TLR4-deficient mice, or TLR2-deficient mice fed a high fat diet during the 150 minute duration of the test (FIG. 7D).

Example 8

Figure 8:
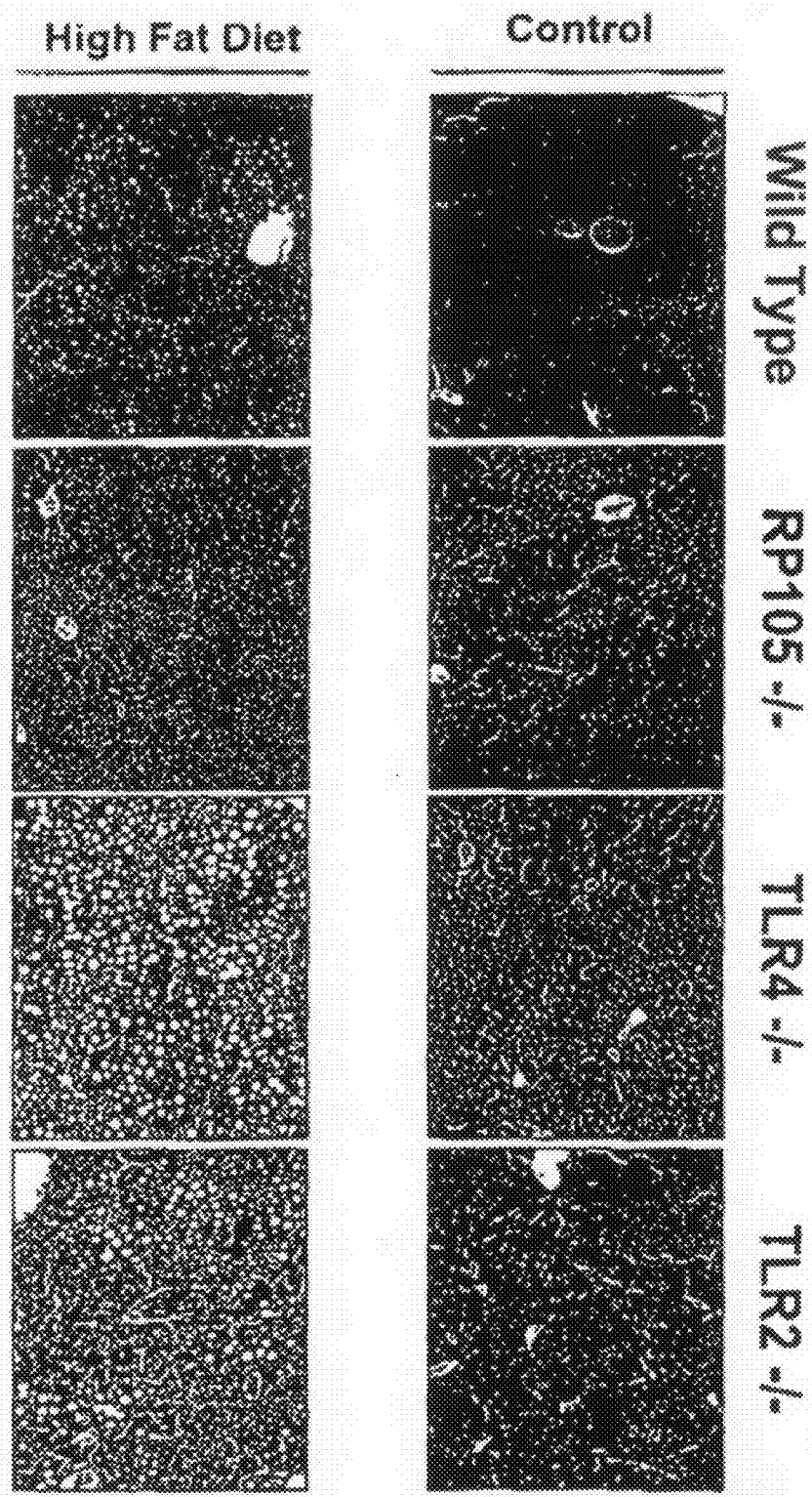
FIG. 8 illustrates protection from high fat diet-induced hepatic steatosis and steatohepatitis in RP105-deficient mice, and exacerbation of high fat diet-induced hepatic steatosis and steatohepatitisin TLR4-deficient and TLR2-deficient mice, compared to wild type mice.

This example illustrates protection from high fat diet-induced hepatic steatosis and steatohepatitis in RP105-deficient mice, exacerbated hepatic steatosis and steatohepatitis TLR4-deficient and TLR2-deficient, compared with wild type mice In these experiments, fully backcrossed RP105-deficient, TLR4-deficient and TLR2-deficient mice and wild type mice were fed either a regular chow control diet or a high fat diet as described above, and liver tissue samples were examined histologically. As shown in FIG. 8, tissue from wild type mice fed a high fat diet exhibited accumulation of fat droplets indicative of steatosis, along with infiltration of inflammatory cells indicative of steatohepatitis. Both steatosis and steatohepatitis was worse in liver tissue samples from TLR4-deficient and TLR2-deficient. mice. In contrast, tissue samples from RP105-deficient mice fed a high fat diet exhibited neither steatosis nor steatohepatitis, and were histologically similar to tissue samples obtained from mice fed a control diet.

These observations demonstrate that RP105-deficient mice are protected from steatosis and steatohepatitis compared to wild type. TLR4-deficient or TLR2-deficient mice fed a high fat diet, and imply that inhibition of RP105 activity can reduce the development of steatosis and steatohepatitis, sequelae of diet-induced obesity.

Example 9

This example illustrates that RP105 siRNA inhibits surface expression of RP105 in HEK293 cells.

Figure 9:
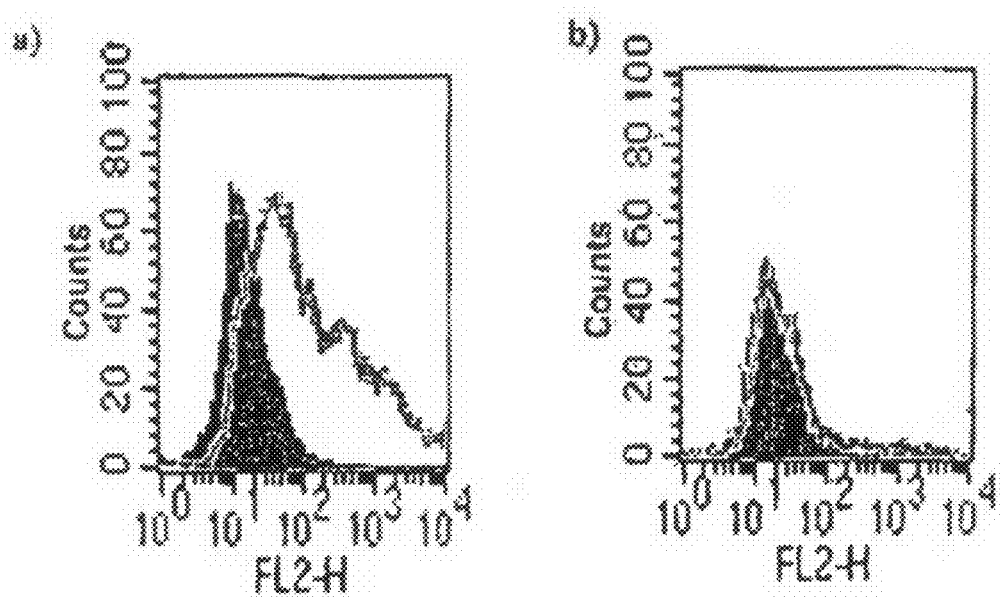
FIG. 9 illustrates ability to inhibit RP105 expression using siRNA mediated techniques

In this example, a 750 bp DNA fragment of huRP105 (from bp 1022 to 1748) was amplified by PCR, converted to dsRNA using T7 polymerase, digested in vitro with Dicer enzyme using the GeneSilencer siRNA Transfection Kit (Gene Therapy Systems, San Diego, Calif.). HEK293 cells were cultured in polystyrene, sterile, non-pyrogenic 48 well plates (Corning Inc., Corning, N.Y.) for 24 hours. HEK293 cells were transiently transfected with siRNA using GeneSilencer siRNA Transfection Reagent (Gene Therapy Systems, San Diego, Calif.) according to manufacturer's instructions, (a) MD-1 cDNA (1 µg) or (b) MD-1 cDNA (1 µg) plus RP105 siRNA (250 ng). 48 hours following the transfection, cells were collected and stained with phycoerythrin labeled monoclonal mouse anti-human RP105 antibody (e-Bioscience, San Diego, Calif.) and analyzed for RP105 surface expression by flow cytometry (FACS Calibur, Becton Dickinson, San Diego, Calif.). The data (FIG. 9) indicate that cell surface expression of RP105 was inhibited in cells transfected with MD-1 cDNA plus R105 siRNA.

All cited references are incorporated herein by reference as if fully set forth.

What is claimed is:

1. A method of treating or preventing diet-induced obesity and/or one or more sequelae thereof in a subject, the method comprising administering to a subject in need of treatment or at risk for developing diet-induced obesity and/or one or more sequelae thereof, a therapeutically effective amount of a pharmaceutical composition comprising at least one inhibitor of RP105 expression and/or MD-1 expression, wherein the at least one inhibitor of RP105 and/or MD-1 expression is at least one shRNA or siRNA, or a precursor thereof, and wherein the at least one precursor comprises a sequence selected from the group consisting of CCTCTTGGTCTC-CAGAGTCAGGCATTCAA (SEQ ID NO: 1); CTACCT-CAATCTGGCTGCCAACAGCATTA (SEQ ID NO: 2); CATCAACCTAAGCCTGAACTTCAATGGCA (SEQ ID NO: 3); and GCAGGAACACCGCTTCTCTGACATCTCAT (SEQ ID NO: 4).

* * * * *

UNITED STATES PATENT AND TRADEMARK OFFICE
CERTIFICATE OF CORRECTION

PATENT NO. : 8,404,656 B2
APPLICATION NO. : 12/672869
DATED : May 3, 2011
INVENTOR(S) : Christopher L. Karp et al.

It is certified that error appears in the above-identified patent and that said Letters Patent is hereby corrected as shown below:

In the Specifications:

Page 11, Column 1, lines 13-16; delete "The invention was developed at least in part with the support of NIH grants R21 AI063183, R01 AI075159, and 5P30AR047363. The US government has certain rights in the invention." and insert --This invention was made with government support under AI063183, AR047363, and AI075159 awarded by the National Institutes of Health. The government has certain rights in the invention.--

Signed and Sealed this
Fourteenth Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,404,656 B2
APPLICATION NO. : 12/672869
DATED : March 26, 2013
INVENTOR(S) : Karp et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 275 days.

Signed and Sealed this
First Day of September, 2015

Michelle K. Lee
*Director of the United States Patent and Trademark Office*

SEQUENCE LISTING

```
<160> NUMBER OF SEQ ID NOS: 6

<210> SEQ ID NO 1
<211> LENGTH: 29
<212> TYPE: DNA
<213> ORGANISM: Homo sapiens

<400> SEQUENCE: 1
cctcttggtc tccagagtca ggcattcaa                                29

<210> SEQ ID NO 2
<211> LENGTH: 29
<212> TYPE: DNA
<213> ORGANISM: Homo sapiens

<400> SEQUENCE: 2
ctacctcaat ctggctgcca acagcatta                                29

<210> SEQ ID NO 3
<211> LENGTH: 29
<212> TYPE: DNA
<213> ORGANISM: Homo sapiens

<400> SEQUENCE: 3
catcaaccta agcctgaact tcaatggca                                29

<210> SEQ ID NO 4
<211> LENGTH: 29
<212> TYPE: DNA
<213> ORGANISM: Homo sapiens

<400> SEQUENCE: 4
gcaggaacac cgcttctctg acatctcat                                29

<210> SEQ ID NO 5
<211> LENGTH: 2725
<212> TYPE: DNA
<213> ORGANISM: Homo sapiens

<400> SEQUENCE: 5
agaatgctga gcagtcaaca gcatttcttg ttccaagatc acccttctga gtacctctct     60
ggctgccaaa ttgccagggc cttcacagtt tgattccatt tctcagctcc aagcattagg    120
taaacccacc aagcaatcct agcctgtgat ggcgtttgac gtcagctgct tcttttgggt    180
ggtgctgttt tctgccggct gtaaagtcat cacctcctgg gatcagatgt gcattgagaa    240
agaagccaac aaaacatata actgtgaaaa tttaggtctc agtgaaatcc ctgacactct    300
accaaacaca acagaatttt tggaattcag ctttaatttt ttgcctacaa ttcacaatag    360
aaccttcagc agactcatga atcttacctt tttggattta actaggtgcc agattaactg    420
gatacatgaa gacactttc aaagccatca tcaattaagc acacttgtgt taactggaaa     480
tcccctgata ttcatggcag aaacatcgct taatgggccc aagtcactga agcatctttt    540
cttaatccaa acgggaatat ccaatctcga gtttattcca gtgcacaatc tggaaaactt    600
ggaaagcttg tatcttggaa gcaaccatat ttcctccatt aagttcccca aagcttccc     660 agcacggaat ctgaaagtac tggattttca gaataatgct atacactaca tctctagaga    720
agacatgagg tctctggagc aggccatcaa cctaagcctg aacttcaatg caataatgt     780
```

```
taaaggtatt gagcttgggg cttttgattc aacgatcttc caaagtttga actttggagg        840
aactccaaat ttgtctgtta tattcaatgg tctgcagaac tctactactc agtctctctg        900
gctgggaaca tttgaggaca ttgatgacga agatattagt tcagccatgc tcaagggact        960
ctgtgaaatg tctgttgaga gcctcaacct gcaggaacac cgcttctctg acatctcatc       1020
caccacattt cagtgcttca cccaactcca agaattggat ctgacagcaa ctcacttgaa       1080
agggttaccc tctgggatga agggtctgaa cttgctcaag aaattagttc tcagtgtaaa       1140
tcatttcgat caattgtgtc aaatcagtgc tgccaatttc ccctccctta cacacctcta       1200
catcagaggc aacgtgaaga aacttcacct tggtgttggc tgcttggaga aactaggaaa       1260
ccttcagaca cttgatttaa gccataatga catagaggct tctgactgct gcagtctgca       1320
actcaaaaac ctgtcccact tgcaaacctt aaacctgagc cacaatgagc ctcttggtct       1380
ccagagtcag gcattcaaag aatgtcctca gctagaactc ctcgatttgg catttacccg       1440
cttacacatt aatgctccac aaagtccctt ccaaaacctc catttccttc aggttctgaa       1500
tctcacttac tgcttccttg ataccagcaa tcagcatctt ctagcaggcc taccagttct       1560
ccggcatctc aacttaaaag ggaatcactt tcaagatggg actatcacga agaccaacct       1620
acttcagacc gtgggcagct tggaggttct gattttgtcc tcttgtggtc tcctctctat       1680
agaccagcaa gcattccaca gcttgggaaa aatgagccat gtagacttaa gccacaacag       1740
cctgacatgc gacagcattg attctcttag ccatcttaag ggaatctacc tcaatctggc       1800
tgccaacagc attaacatca tctcaccccg tctcctccct atcttgtccc agcagagcac       1860
cattaattta agtcataacc ccctggactg cacttgctcg aatattcatt tcttaacatg       1920
gtacaaagaa aacctgcaca aacttgaagg ctcggaggag accacgtgtg caaacccgcc       1980
atctctaagg ggagttaagc tatctgatgt caagcttttcc tgtgggatta cagccatagg       2040
cattttcttt ctcatagtat ttctattatt gttggctatt ctgctatttt ttgcagttaa       2100
ataccttctc aggtggaaat accaacacat ttagtgctga aggtttccag agaaagcaaa       2160
taagtgtgct tagcaaaatt gctctaagtg aaagaactgt catctgctgg tgaccagacc       2220
agacttttca gattgcttcc tggaactggg cagggactca ctgtgctttt ctgagcttct       2280
tactcctgtg agtcccagag ctaaagaacc ttctaggcaa gtacaccgaa tgactcagtc       2340
cagagggtca gatgctgctg tgagaggcac agagcccttt ccgcatgtgg aagagtggga       2400
ggaagcagag ggagggactg ggcagggact gccggcccg gagtctccca cagggaggcc       2460 attcccttc tactcaccga catccctccc agcaccacac accccgcccc tgaaaggaga       2520
tcatcagccc ccacaatttg tcagagctga agccagccca ctaccaccc ccactacagc       2580 attgtgcttg ggtctgggtt ctcagtaatg tagccatttg agaaacttac ttggggacaa       2640
agtctcaatc cttatttaa atgaaaaaag aaaagaaaag cataataaat ttaaaagaaa       2700
aggctgagaa atgaaaaaaa aaaaa                                            2725
```

<210> SEQ ID NO 6
<211> LENGTH: 905
<212> TYPE: DNA
<213> ORGANISM: Homo sapiens

<400> SEQUENCE: 6

```
ccacgcgtcc gtgttttctc gtgtgtccca tacaggcccc caccatgaag ggtttcacag         60
ccactctctt cctctggact ctgattttc ccagctgcag tggaggcggc ggtgggaaag        120
cctggcccac acacgtggtc tgtagcgaca gcggcttgga agtgctctac cagagttgcg        180
```

```
atccattaca agattttggc ttttctgttg aaaagtgttc caagcaatta aaatcaaata    240
tcaacattag atttggaatt attctgagag aggacatcaa agagcttttt cttgacctag    300
ctctcatgtc tcaaggctca tctgttttga atttctccta tcccatctgt gaggcggctc    360
tgcccaagtt ttctttctgt ggaagaagga aaggagagca gatttactat gctgggcctg    420
tcaataatcc tgaatttact attcctcagg gagaatacca ggttttgctg gaactgtaca    480
ctgaaaaacg gtccaccgtg gcctgtgcca atgctactat catgtgctcc tgactgtggc    540
ctgtagcaaa aatcacagcc agctgcatct cgtgggacct ccaagctcct ctgactgaac    600
ctactgtggg aggagaagca gctgatgaca gagagaggct ctacaaagaa gcgcccccaa    660
agagtgcagc tgctaatttt agtcccagga ccagacatcc ccagactcca cagatgtaat    720
gaagtccccg aatgtatctg tttctaagga gcctcttggc agtccttaag cagtcttgag    780
ggtccatcct ttttctctaa ttggtcgcct cccaccagac tcacctgctt ttcaactttt    840
taggagtgct tcctcacagt taccaagaat aaagaaagct ggccaccata aaaaaaaaaa    900
aaaaa                                                                905
```